United States Patent
Kagawa et al.

(10) Patent No.: US 7,037,092 B2
(45) Date of Patent: May 2, 2006

(54) ROLLER PUMP WITH HOUSING HAVING INTEGRATED REDUCTION GEAR HOUSING

(75) Inventors: Yoshihisa Kagawa, Yono (JP); Kazuhide Yamazaki, Yono (JP); Seiji Kojima, Kiryu (JP)

(73) Assignee: Japan Servo Co., Ltd., Tokyo (JP)

( * ) Notice: Subject to any disclaimer, the term of this patent is extended or adjusted under 35 U.S.C. 154(b) by 467 days.

(21) Appl. No.: 10/092,524

(22) Filed: Mar. 8, 2002

(65) Prior Publication Data

US 2002/0131881 A1    Sep. 19, 2002

(30) Foreign Application Priority Data

Mar. 13, 2001 (JP) .............................. 2001-069786

(51) Int. Cl.
*F04B 43/08* (2006.01)

(52) U.S. Cl. ................ 417/746; 417/477.7; 417/477.9; 417/477.1

(58) Field of Classification Search ................ 417/476, 417/477.9, 477.7, 477.1, 313, 423.6
See application file for complete search history.

(56) References Cited

U.S. PATENT DOCUMENTS

| 3,644,068 | A | * | 2/1972 | Lepak | 417/477.7 |
| 3,885,894 | A | * | 5/1975 | Sikes | 417/477.1 |
| 3,963,023 | A | * | 6/1976 | Hankinson | 604/19 |
| 4,558,996 | A | * | 12/1985 | Becker | 417/374 |
| 4,969,808 | A | * | 11/1990 | Tsukada | 417/477.1 |
| 5,387,088 | A | * | 2/1995 | Knapp et al. | 417/53 |
| 5,929,589 | A | * | 7/1999 | Suzuki et al. | 318/685 |
| 2002/0001527 | A1 | * | 1/2002 | Beller et al. | 417/300 |

FOREIGN PATENT DOCUMENTS

| GB | 2051253 A | * | 1/1981 |
| JP | 360088885 A | * | 5/1985 |

* cited by examiner

*Primary Examiner*—Charles G. Freay
*Assistant Examiner*—Emmanuel Sayoc
(74) *Attorney, Agent, or Firm*—Birch, Stewart, Kolasch & Birch, LLP

(57) ABSTRACT

A roller pump comprises a pump housing having a cylindrical inner surface, a rotor fixed to a drive shaft placed at the central portion of the pump housing, rollers provided around the rotor and a driver for driving the drive shaft through a reduction gear. The rollers press an elastic tube installed between the rollers and the inner surface of the pump housing to transfer a liquid in the elastic tube by rotation of the rotor. The pump housing and the reduction gear are integrated into one body and an output shaft of the reduction gear is fixed to the drive shaft of the rotor. A stepping motor is used as the driver. A part of the inner surface of the pump housing is composed of a semicircle, another part of the inner surface is composed of a partial circle of which center is shifted from the center of the semicircle. The inlet and outlet slots are provided with levers for pressing the inlet or outlet portion into the inlet or outlet slot to hold inlet or outlet portion in the inlet or outlet slot respectively.

16 Claims, 2 Drawing Sheets

ROLLER PUMP WITH HOUSING HAVING INTEGRATED REDUCTION GEAR HOUSING

BACKGROUND OF THE INVENTION

1. Field of the Invention

The present invention concerns a roller pump that performs pumping action pressing an elastic tube installed in the roller pump with a roller rotation apparatus. Particularly, the present invention concerns an improvement of such a roller pump suitable for medical application.

2. Description of the Prior Art

In a roller pump of the prior art, a brushless DC motor (for example) is used as a driver that drives the roller pump through a reduction gear with a comparatively large reduction ratio.

Such reduction gear generally comprises a gear train assembled in a separated independent case.

A pump housing, the reduction gear and the motor, each manufactured separately, are connected to compose the roller pump.

An inner surface of the pump housing has a cylindrical form. This cylindrical form is rather complicated. It has a progressively longer radius in the vicinity of inlet and outlet portions of an elastic tube installed along the inner surface of the pump housing, in comparison with the radius in the vicinity of a central portion of the elastic tube, in order to suppress pulsatory motion of a liquid being transferred from the inlet portion toward the outlet portion of the elastic tube.

Further, inlet and outlet slots to insert and fix the inlet and the outlet portions of the elastic tube respectively, and to suppress vibration of the elastic tube during operation, are provided with the pump housing. To install the elastic tube into the pump housing, the inlet and the outlet portions of the elastic tube are inserted and fixed in the inlet and the outlet slots of the pump housing respectively.

In order to make it possible to fix the inlet and the outlet portions of the elastic tube with a different size to the inlet and the outlet slots of the pump housing respectively, such as fixing adapters or levers with springs are used. In the case of the latter, the lever is manually operated to fix each of the inlet and the outlet portions of the elastic tube in the inlet and the outlet slots of the pump housing respectively.

In the roller pump of the prior art as described above, there is a problem that the roller pump comprises a large number of parts and is expensive, since the reduction gear and the pump housing are manufactured separately.

Also in the roller pump of the prior art in which a brushless DC motor is used as the driver, there is a problem that gears of the reduction gear cause a large noise, the gears wear in a comparatively short period, and a large force is required to manually rotate the rotor when it is necessary, since the brushless DC motor is operated at a comparatively high rotation speed that is reduced to a suitable rotation speed for the rotary pump by a reduction gear with a comparatively large reduction ratio.

Also in the roller pump of the prior art in which a stepping motor without a rotation sensor is used as the driver, there is a problem that the efficiency is rather low and a large noise is generated, since it is necessary to use a stepping motor with a larger power than the power required for the rotary pump, in order to prevent such stepping motor from stepping out.

Further, in the roller pump of the prior art, there is a problem that the roller pump is difficult to be manufactured, and therefore it is expensive, since the inner surface of the pump housing has a complicated cylindrical form having a progressively longer radius in the vicinity of the inlet and the outlet portions of the elastic tube installed along the inner surface of the pump housing, in comparison with the radius in the vicinity of the central portion of the elastic tube, in order to suppress pulsatory motion of the liquid being transferred from the inlet portion toward the outlet portion of the elastic tube.

Further, in the roller pump of the prior art in which the fixing adapters corresponding to the size of the elastic tube are used for inserting and fixing the inlet and the outlet portions of the elastic tube to the inlet and the outlet slots of the pump housing respectively, there is a problem that the fixing adapter is often removed together with the elastic tube when only the latter is to be removed.

Also in the roller pump of the prior art in which the levers with springs are used for fixing the inlet and the outlet portions of the elastic tube to the inlet and the outlet slots of the pump housing respectively, there is a problem that the installing operation of the elastic tube is troublesome, since it is necessary to grasp the elastic tube with one hand and handle the lever with another hand.

SUMMARY OF THE INVENTION

It is an object of the present invention to provide a roller pump capable of reducing costs by reducing the number of parts composing the roller pump sharply.

It is another object of the present invention to provide a roller pump capable of reducing the rotation speed of the drive source, lowering the reduction ratio of the reduction gears, that can be controlled from a low rotation speed to a high rotation speed without stepping out, and of which vibration and noise are low.

It is a further object of the present invention to provide a roller pump capable of reducing a lashing noise of gears and pulsating motion in the pumping action, at a low cost.

It is another object of the present invention to provide a roller pump easy for installing an elastic tube.

To achieve the above objects, the roller pump according to the present invention comprises a pump housing having a cylindrical inner surface, a rotor fixed to a drive shaft placed at the central portion of the pump housing, rollers provided around the rotor and a driver for driving the drive shaft through a reduction gear. The rollers press an elastic tube installed between the roller and the inner surface of the pump housing toward the inner surface to transfer a liquid in the elastic tube in a direction, being rotated by the rotor to move the place where the rollers press the elastic tube. The pump housing and the reduction gear are integrated into one body and an output shaft of the reduction gear is fixed to the drive shaft of the rotor.

By constructing the pump housing and the reduction gear in one body, number of parts, and consequently the cost, can be sharply reduced.

Further, to achieve the above objects, a stepping motor provided with a rotation sensor that is roll controllable is used as the driver.

By using the stepping motor provided with the rotation sensor, the rotation speed of the driver can be lowered, the reduction ratio can be made smaller, and thus the roller pump is controllable in wide range from a low rotation speed to a high rotation speed, of which vibration and noise are low, can be realized.

Further, to achieve the above objects, a part of the inner surface of the pump housing is composed of a semicircle of which center coincides with the center of the drive shaft, another part of the inner surface is composed of a partial circle of which center is shifted from the center of the drive shaft, and of which the length of radius is equal to that of the semicircle. Each of end portions of the semicircle and each of end portions of the partial circle are connected by each of tangential lines extending from each of the end portions of the semicircle toward each of the end portions of the partial circle respectively. The partial circle is made to be a form suitable to be connected to an inlet slot for attaching an inlet portion of the elastic tube, and to an outlet slot for attaching an outlet portion of the elastic tube, respectively.

Alternatively, a part of the inner surface of the pump housing is composed of a semicircle of which the center coincides with the center of the drive shaft, another part of the inner surface is composed of a partial circle of which center is shifted from the center of the drive shaft, and of which the length of the radius is larger than that of the semicircle. Each of end portions of the semicircle and each of end portions of the partial circle are connected respectively. The partial circle is made to be a form suitable to be connected to an inlet slot for attaching an inlet portion of the elastic tube, and to an outlet slot for attaching an outlet portion of the elastic tube, respectively.

By making the inner surface of the pump housing in the forms as described above, the roller pump capable of reducing the beating sound of gears as well as the pulsation in pumping action can be provided at a low cost.

Further, to achieve the above objects, the inlet slot is provided with a lever for pressing the inlet portion into the inlet slot to hold the inlet portion in the inlet slot. The lever is rotated perpendicularly to the axis of the elastic tube by a spring force to press the inlet portion of the elastic tube, and an upper end portion of the lever is tilted relative to the vertical axis. The inlet portion is attached to the pump housing being pushed downward through a place between the upper end portion and the inlet slot. Also, the outlet slot is provided with a lever for pressing the outlet portion into the outlet slot to hold the outlet portion in the outlet slot. The lever is rotated perpendicularly to the axis of the elastic tube by a spring force to press the outlet portion of the elastic tube, an upper end portion of the lever is tilted relative to the vertical axis. The outlet portion is attached to the pump housing being pushed downward through a place between the upper end portion and the outlet slot.

By providing such levers to the inlet and outlet slots, installing of the elastic tube can be made easily.

DETAILED DESCRIPTION OF THE INVENTION

Preferred embodiments of the roller pump according to the present invention are explained referring to the attached drawings.

Figure 1:
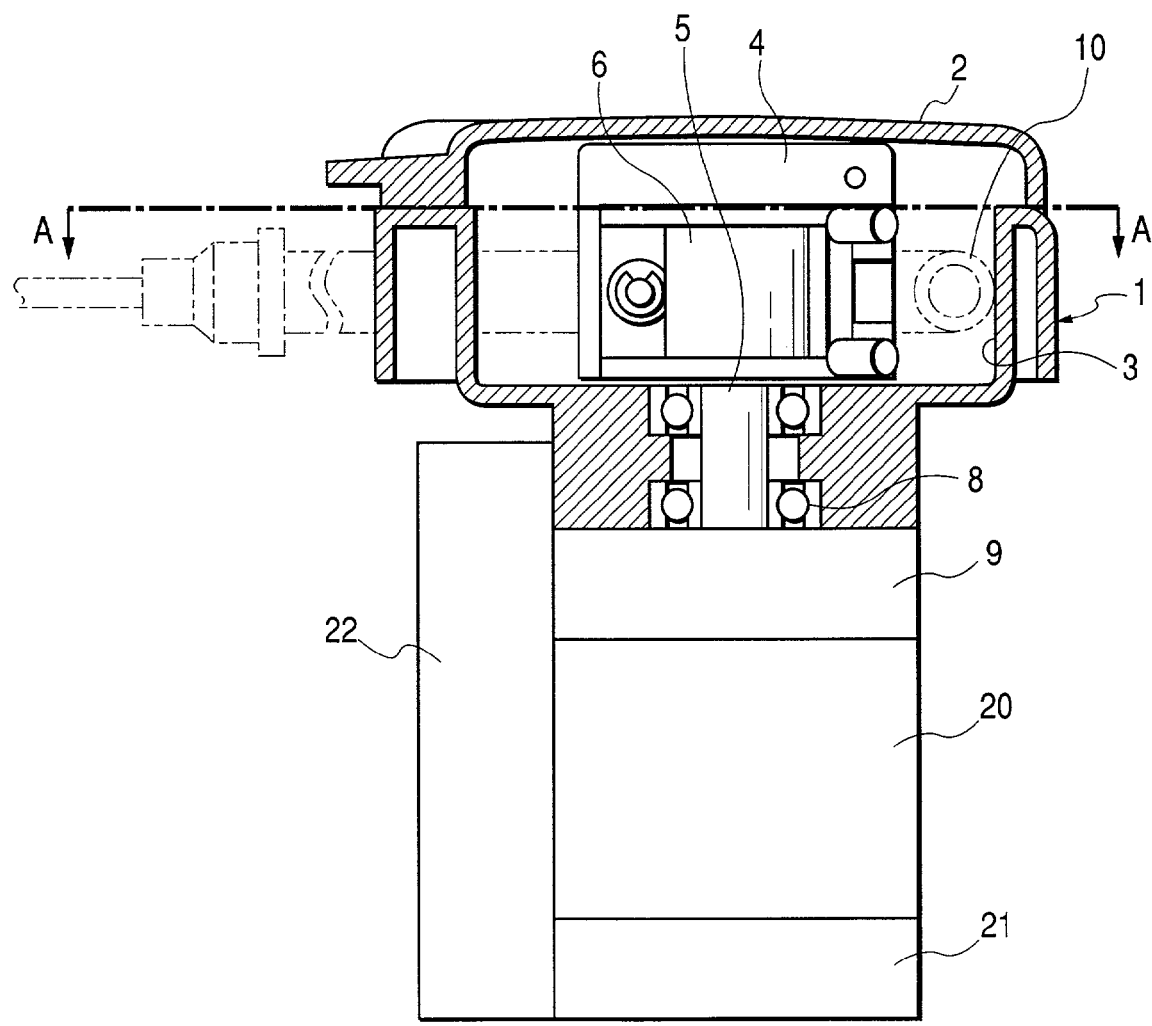
FIG. 1 is a longitudinal sectional view showing the principal part of the roller pump according to the present invention.

FIG. 1 is a longitudinal sectional view showing the principal part of the roller pump according to the present invention.

Figure 2:
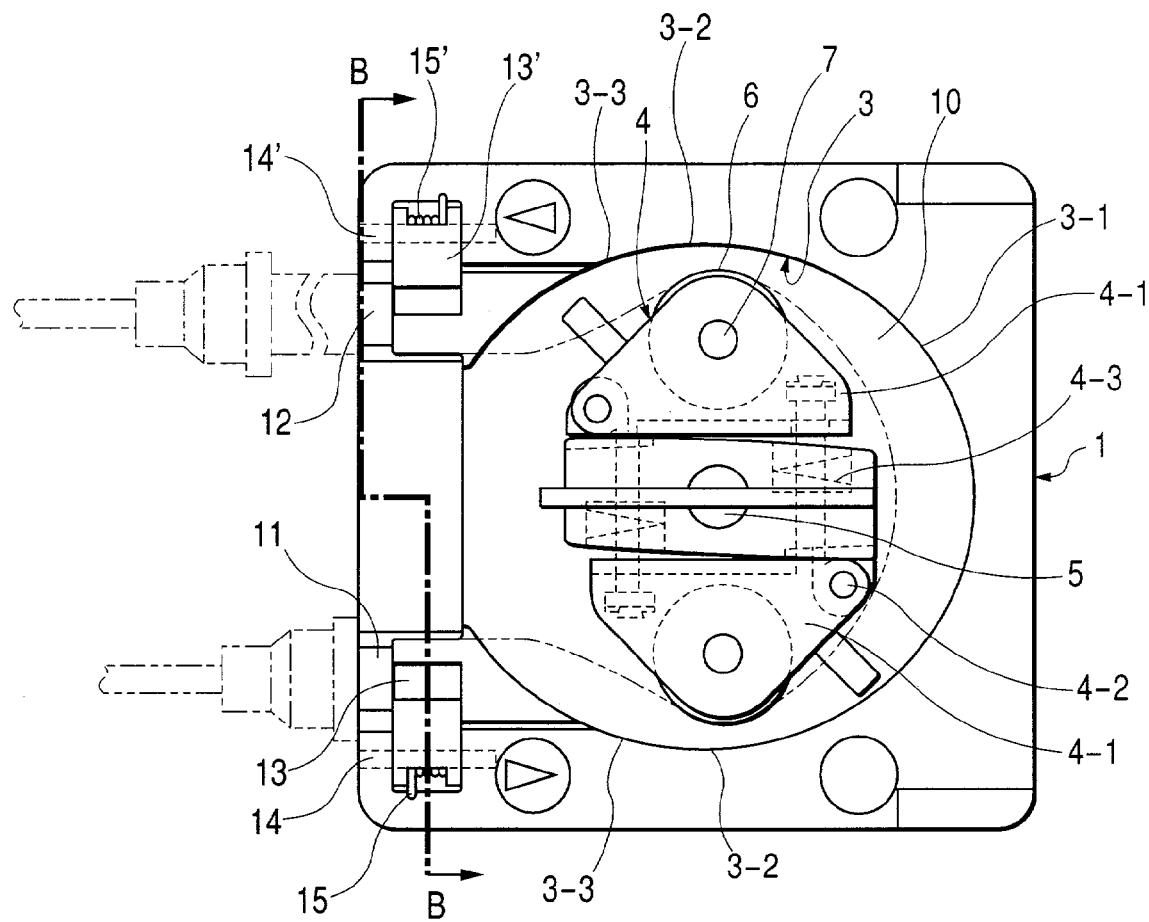
FIG. 2 is a horizontal sectional view along A—A line in FIG. 1.

FIG. 2 is a horizontal sectional view along A—A line in FIG. 1.

Figure 3:
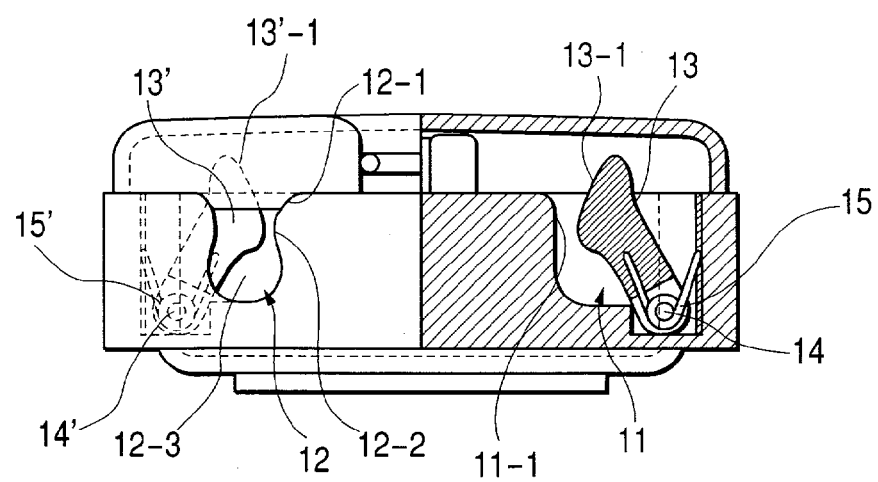
FIG. 3 is a sectional side elevation along B—B line in FIG. 2.

FIG. 3 is a sectional side elevation along B—B line in FIG. 2.

In FIGS. 1 and 2, 1 is a pump housing, 2 is a cover of the pump housing 1, 3 is an inner surface of the pump housing 1, 4 is a rotor, 5 is a rotor shaft that is a drive shaft of the rotor 4, 6 is a roller, 7 is a roller shaft, 8 is a bearing, 9 is a reduction gear, 10 is an elastic tube, 11 is an inlet slot, 12 is an outlet slot, 13:13' are levers for holding the elastic tube 10, 14,14' are shafts of the levers 13,13' respectively, 15,15' are springs for applying rotational forces to the levers 13, 13' respectively, 20 is a stepping motor, 21 is a rotation sensor for the stepping motor 20 and 22 is a drive control circuit of the stepping motor 20.

Construction of the rotor 4 is now explained in detail referring to FIGS. 1 and 2.

The central portion of the rotor 4 is fixed to the rotor shaft 5. The rotor 4 comprises two roller supporting plates 4-1 of a triangular shape, each placed at a symmetrical position with regard to the rotor shaft 5. A side end of the roller supporting plate 4-1 is rotatably attached to the rotor 4 with one of support shafts 4-2 parallel with each other. Another side end of the roller supporting plate 4-1 is provided with a spring 4-3 that pushes the roller supporting plate 4-1 outwardly to rotate it around the support shaft 4-2. The roller 6 is rotatably attached to the each external end portion of the roller supporting plate 4-1 with the roller shaft 7 parallel to the rotor shaft 5. A periphery of the roller 6 is partially protruding out of the roller supporting plate 4-1. The roller 6 is pressed outwardly by the spring 4-3 through the roller supporting plate 4-1 and presses the elastic tube 10 installed between the inner surface 3 of the pump housing 1 and the rotor 4.

As shown In FIG. 1, two bearings 8 for supporting the rotor shaft 5 are provided in the lower part of the pump housing 1. The rotor 4 is fixed to an upper end portion of the rotor shaft 5. The reduction gear 9 is installed under the rotor shaft 5. The stepping motor 20 is installed under the reduction gear 9. A lower end portion of the rotor shaft 5 is connected to the stepping motor 20 through the reduction gear 9. Driving force of the stepping motor 20 is transmitted to the rotor shaft 5 through the reduction gear 9.

The rotation sensor 21 is provided with the stepping motor 20.

As shown in FIGS. 1 and 2, the inner surface 3 of the pump housing 1 is formed in a cylindrical form and has a height capable of receiving the rotor 4 in it. The inlet slot 11 and the outlet slot 12 for holding an inlet portion and an outlet portion of the elastic tube 10 respectively are provided at a side end portion of the pump housing 1. The elastic tube 10 is installed in the pump housing 1 along the inner surface 3 in a U-shape with the inlet portion and the outlet portion held in the inlet slot 11 and in the outlet slot 12 respectively.

Referring to FIG. 2, a horizontal section of the right portion (the portion where the inlet slot 11 and the outlet slot 12 are not formed) of the inner surface 3 of the pump housing 1 is composed of a semicircle 3-1 having a radius r, the center of which coincides with the center of the rotor shaft 5. A horizontal section of the left portion (the portion where the inlet slot 11 and the outlet slot 12 are formed) of the inner surface 3 of the pump housing 1 is composed of a partial circle 3-3 having also a radius r, the center of which is shifted to the left of the center of the rotor shaft 5. Each end of the semicircle 3-1 and each end of the partial circle 3-3 are connected by each tangential line of the semicircle 3-1 extending from each end of the semicircle 3-1 toward each end of the partial circle 3-3, respectively. In other words, the horizontal section of the inner surface 3 presents an ellipse-like form made of the semicircle 3-1 and the partial circle 3-3 having the same radius r, the centers of which are shifted with each other, and the each end of which is connected with each other by each tangential line 3-2. Additionally, the left portion of the partial circle 3-3 are formed into an appropriate form to be connected to the inlet slot 11 and the outlet slot 12.

The elastic tube 10 is pressed by the two rollers 6 toward the inner surface 3 of the pump housing 1 thus formed. Accordingly, the inner side of the elastic tube 10 presents a form shown by a two-dot chain line in FIG. 2. As the upper roller 6 in FIG. 2 moves toward the left, the roller 6 that has been opposing to the tangential line 3-2 of the inner surface 3 of the pump housing 1 comes to oppose the partial circle 3-3. Since the center of the partial circle 3-3 is shifted to the left by the length of the tangential line 3-2, the distance between the inner surface 3 of the pump housing 1 and the roller 6 becomes longer, and the pushing force of the roller 6 against the elastic tube 10 becomes weaker. As the pushing force of the roller 6 against the elastic tube 10 becomes weaker, a repellent force in the rotating direction applied to the roller 6 by the elastic tube 10 at the time when the roller 6 departs from the elastic tube 10 also becomes weaker. Accordingly, the noise generated in the reduction gear 9 can be reduced.

At the time when the lower roller 6 in FIG. 2 begins to contact the elastic tube 10, the roller 6 contacts the portion of the elastic tube 10 in the partial circle 3-3. As the rotor 4 rotates counter-clockwise, the distance between the roller 6 and the inner surface 3 of the pump housing 1 becomes gradually shorter, then the distance becomes minimum at the point of contact of the tangential line 3-2 with the semicircle 3-1. After that, the distance remains constant during 180 degrees rotation of the rotor 4. Accordingly, the torque required for rotating the rotor 4 gradually increases, then becomes the maximum and remains constant during 180 degrees rotation of the rotor 4. Consequently, the variable component of the force applied to the gears of the reduction gear 9 as well as to the stepping motor 20 is small, the noise generated is low, and the life of the gears of the reduction gear 9 can be lengthened.

In place of the form of the inner surface 3 as described above another form of the inner surface 3 in which another partial circle 3-3 having a radius slightly longer than that of the semicircle 3-1, and the center of which is shifted to the left of the center of the rotor shaft 5, is used to connect the each end of the semicircle 3-1 with the inlet slot 11 or the outlet slot 12 respectively.

Also in this form of the inner surface 3, the distance between the roller 6 and the inner surface 3 increases gradually as the roller 6 moves from the end portion of the semicircle 3-1 toward the outlet portion of the elastic tube 10 and decreases gradually as the roller 6 moves from the inlet portion of the elastic tube 10 toward the end portion of the semicircle 3-1. Consequently, the noise generated by the reduction gear 9 can be reduced and the life of the gears of the reduction gear 9 can be lengthened, similarly to the embodiment described above.

A form of the outlet slot 12 is shown in FIG. 3. As shown in the drawing, an upper portion 12-1 and a lower portion 12-3 of the outlet slot 12 are formed to be comparatively wide in width, whereas a mid portion 12-2 of the outlet slot 12 is formed to be comparatively narrow in width. Thus formed outlet slot 12 enables an easy insertion, as well as prevention from falling-off, of the outlet portion of the elastic tube 10 having an external diameter of various size. Additionally, the inlet slot 11 is also formed similarly to the outlet slot 12, which also has the same effects as those of the outlet slot 12.

As shown in FIGS. 2 and 3, a lever 13 for pressing and holding the inlet portion of the elastic tube 10 is provided to the out side of the inlet slot 11. Similarly, a lever 13' for pressing and holding the outlet portion of the elastic tube 10 is provided to the out side of the outlet slot 12. The lever 13 is rotatably attached to the inlet slot 11 with a shaft 14 parallel to the inlet slot 11. Similarly, the lever 13' is attached to the outlet slot 12 with a shaft 14' parallel to the outlet slot 12. The lever 13 is provided with a spring 15 that makes the lever 13 press the inlet portion of the elastic tube 10 in the inlet slot 11, toward the inner portion of the inlet slot 11. Also, the lever 13' is provided with a spring 15 that makes the lever 13' press the outlet portion of the elastic tube 10 in the outlet slot 12, toward the inner portion of the outlet slot 12. Thus, the inlet portion of the elastic tube 10 is pressed toward the inlet slot 11 and is held there. Also, the outlet portion of the elastic tube 10 is pressed toward the outlet slot 12 and is held there.

As shown in FIG. 3, upper end portions 13-1,13'-1 of the levers 13 are tilted relative to the vertical axis and form a part of V-shape. The inlet portion of the elastic tube 10 is pushed into a place between the mid portion (not shown in the drawing) of the inlet slot 11 and the upper end portion 13-1 of the lever 13, then the tilted upper end portion 13-1 is rotated toward the right opposing to the spring force of the spring 15 and allows the inlet portion of the elastic tube 10 to pass through into the inlet slot 11. Similarly, the outlet portion of the elastic tube 10 is pushed into a place between the mid portion 12-2 of the outlet slot 12 and the upper end portion 13'-1 of the lever 13', then the tilted upper end portion 13'-1 is rotated toward the left opposing to the spring force of the spring 15 and allows the outlet portion of the elastic tube 10 passing through into the outlet slot 12. As inlet portion and the outlet portion enter into the inlet slot 11 or outlet slot 12 respectively, they are pressed into the inlet slot 11 or outlet slot 12 respectively, and the elastic tube 10 is prevented from falling off.

Such operation of attaching the inlet and outlet portions of the elastic tube 10 to the inlet slot 11 or outlet slot 12 can be handled by one hand in one action. Comparing with the roller pump of the prior art in which such operation needs to be handled by two hands, the roller pump according to the present invention is easier to be handled.

To install the elastic tube 10 of the roller pump according to the present invention, a cover 2 (see FIG. 1) rotatably attached to the pump housing 1 is opened, then the inlet portion of the elastic tube 10 is fixed to the inlet slot 11 of the pump housing 1 in the manner as explained above, and then the elastic tube 10 is laid in the pump housing 1 in a U-shape, passing through the place between the roller 6 and the inner surface 3 of the pump housing 1. Then, the outlet portion of the elastic tube 10 is fixed to the outlet slot 12 of the pump housing 1, also in the manner as explained above, and then the cover 2 is closed.

The roller pump according to the present invention is operated as follows. First, a pulse current of a predetermined pulse number is transmitted from the drive control circuit 22 into the stepping motor 20. Upon receiving the pulse current, the stepping motor 20 starts to rotate. The rotation of the stepping motor 20 is transmitted to the rotor 4 through the reduction gear 9. As the rotor 4 rotates, two rollers 6 attached to the rotor 4 rotate pressing the elastic tube 10, by a spring force of the spring 4-3, toward the inner surface 3 of the pump housing 1. As the elastic tube 10 is pressed toward the inner surface 3 of the pump housing 1, the elastic tube 10 is blocked. The place in the elastic tube 10 being blocked is moved with the movement of the rotor 4. Consequently, the liquid in the elastic tube is transferred toward the outlet. Thus, the roller pump carries out the pumping action.

In the embodiment of the roller pump according to the present invention as explained above, the stepping motor 20 with the rotation sensor 22 is used. A stepping motor has a number of magnetic teeth both in a rotor and in a stator and the rotation speed of the stepping motor is controlled by a pulse number of a pulse current applied to the stator. Consequently, the controllable range of the rotation speed is wider than that of a brushless DC motor. Since the stepping motor 20 is used in the roller pump according to the present invention, the controllable range of the amount of the liquid to be transferred by the roller pump can be made wider. Particularly, the operation of the roller pump at low speed is stable.

Further, since the reduction ratio of the reduction gear can be made smaller, a reduction gear of a small size can be easily integrated in the pump housing. Further, since the rotor 4 can be rotated by hand with a small force, the roller pump can be easily handled in such an operation as installing the elastic tube 10 into the pump housing 1 in which it is necessary to rotate the rotor 4 by hand.

Additionally, a reduction gear comprising planetary gears or other gears can be used.

What is claimed is:

1. A roller pump comprising:
    a pump housing having a cylindrical inner surface;
    a reduction gear case having a reduction gear therein;
    a rotor fixed to a drive shaft placed at the central portion of said pump housing;
    a driver for driving said drive shaft through said reduction gear; and
    rollers provided around said rotor, said rollers pressing an elastic tube installed between said rollers and said inner surface of said pump housing, wherein said pump housing and said reduction gear case are formed from a single, one-piece member, and an output shaft of said reduction gear is fixed to said drive shaft of said rotor,
    wherein a part of said inner surface of said pump housing is composed of a semicircle of which center coincides with the center of said drive shaft, another part of said inner surface is composed of a partial circle of which center is shifted from the center of said drive shaft, and of which the length of radius is equal to that of said semicircle, each of end portions of said semicircle and each of end portions of said partial circle are connected by each of tangential lines extending from each of said end portions of said semicircle toward each of said end portions of said partial circle respectively, said partial circle is made to be a form suitable to be connected to an inlet slot for attaching an inlet portion of said elastic tube, and to an outlet slot for attaching an outlet portion of said elastic tube.

2. The roller pump according to claim 1, wherein said driver is a stepping motor provided with a rotation sensor and being roll controllable.

3. The roller pump according to claim 2, wherein said inlet slot is provided with a lever for pressing said inlet portion into said inlet slot to hold said inlet portion in said inlet slot, said lever being rotated perpendicularly to the axis of said elastic tube by a spring force to press said inlet portion of said elastic tube, an upper end portion of said lever is tilted relative to the vertical axis, said inlet portion is attached to said pump housing being pushed downward through a place between said upper end portion and said inlet slot, said outlet slot is provided with a lever for pressing said outlet portion into said outlet slot to hold said outlet portion in said outlet slot, said lever being rotated perpendicularly to the axis of said elastic tube by a spring force to press said outlet portion of said elastic tube, an upper end portion of said lever is tilted relative to the vertical axis, said outlet portion is attached to said pump housing being pushed downward through a place between said upper end portion and said outlet slot.

4. The roller pump according to claim 2, wherein the semicircle is a seamless semicircle and the partial circle is a seamless partial circle.

5. The roller pump according to claim 1, wherein said inlet slot is provided with a lever for pressing said inlet portion into said inlet slot to hold said inlet portion in said inlet slot, said lever being rotated perpendicularly to the axis of said elastic tube by a spring force to press said inlet portion of said elastic tube, an upper end portion of said lever is tilted relative to the vertical axis, said inlet portion is attached to said pump housing being pushed downward through a place between said upper end portion and said inlet slot, and said outlet slot is provided with a lever for pressing said outlet portion into said outlet slot to hold said outlet portion in said outlet slot, said lever being rotated perpendicularly to the axis of said elastic tube by a spring force to press said outlet portion of said elastic tube, an upper end portion of said lever is tilted relative to the vertical axis, said outlet portion is attached to said pump housing being pushed downward through a place between said upper end portion and said outlet slot.

6. The roller pump according to claim 1, wherein the semicircle is a seamless semicircle and the partial circle is a seamless partial circle.

7. A roller pump comprising:
    a pump housing having a cylindrical inner surface;
    a reduction gear case having a reduction gear therein;
    a rotor fixed to a drive shaft placed at the central portion of said pump housing;
    a driver for driving said drive shaft through said reduction gear; and
    rollers provided around said rotor, said rollers pressing an elastic tube installed between said rollers and said inner surface of said pump housing, wherein said pump housing and said reduction gear case are formed from a single, one-piece member, and an output shaft of said reduction gear is fixed to said drive shaft of said rotor,
    wherein a part of said inner surface of said pump housing is composed of a semicircle, a center of which coincides with the center of said drive shaft, another part of said inner surface is composed of a partial circle of which center is shifted from the center of said drive shaft, and of which the length of radius is longer than that of said semicircle, each of end portions of said semicircle and each of end portions of said partial circle are connected respectively, said partial circle is made to be a form suitable to be connected to an inlet slot for attaching an inlet portion of said elastic tube, and to an outlet slot for attaching an outlet portion of said elastic tube.

8. The roller pump according to claim 7, wherein said driver is a stepping motor provided with a rotation sensor and being roll controllable.

9. The roller pump according to claim 8, wherein said inlet slot is provided with a lever for pressing said inlet portion into said inlet slot to hold said inlet portion in said inlet slot, said lever being rotated perpendicularly to the axis of said elastic tube by a spring force to press said inlet portion of said elastic tube, an upper end portion of said lever is tilted relative to the vertical axis, said inlet portion is attached to said pump housing being pushed downward through a place between said upper end portion and said inlet slot, said outlet slot is provided with a lever for pressing said outlet portion into said outlet slot to hold said outlet portion in said outlet slot, said lever being rotated perpendicularly to the axis of said elastic tube by a spring force to press said outlet portion of said elastic tube, an upper end portion of said lever is tilted relative to the vertical axis, said outlet portion is attached to said pump housing being pushed downward through a place between said upper end portion and said outlet slot.

10. The roller pump according to claim 8, wherein the semicircle is a seamless semicircle and the partial circle is a seamless partial circle.

11. The roller pump according to claim 7, wherein said inlet slot is provided with a lever for pressing said inlet portion into said inlet slot to hold said inlet portion in said inlet slot, said lever being rotated perpendicularly to the axis of said elastic tube by a spring force to press said inlet portion of said elastic tube, an upper end portion of said lever is tilted relative to the vertical axis, said inlet portion is attached to said pump housing being pushed downward through a place between said upper end portion and said inlet slot, and said outlet slot is provided with a lever for pressing said outlet portion into said outlet slot to hold said outlet portion in said outlet slot, said lever being rotated perpendicularly to the axis of said elastic tube by a spring force to press said outlet portion of said elastic tube, an upper end portion of said lever is tilted relative to the vertical axis, said outlet portion is attached to said pump housing being pushed downward through a place between said upper end portion and said outlet slot.

12. The roller pump according to claim 7, wherein the semicircle is a seamless semicircle and the particle circle is a seamless partial circle.

13. A roller pump comprising:
a pump housing having a cylindrical inner surface;
a reduction gear case having a reduction gear therein;
a rotor fixed to a drive shaft placed at the central portion of said pump housing;
a driver for driving said drive shaft through said reduction gear; and
rollers provided around said rotor, said rollers pressing an elastic tube installed between said rollers and said inner surface of said pump housing, wherein said pump housing and said reduction gear case are formed from a single, one-piece member, and an output shaft of said reduction gear is fixed to said drive shaft of said rotor,
wherein an inlet slot into which an inlet portion of said elastic tube is inserted to attach said inlet portion to said pump housing is provided, said inlet slot is provided with a lever for pressing said inlet portion into said inlet slot to hold said inlet portion in said inlet slot, said lever being rotated perpendicularly to the axis of said elastic tube by a spring force to press said inlet portion of said elastic tube, an upper end portion of said lever is tilted relative to the vertical axis, said inlet portion is attached to said pump housing by being pushed downward through a place between said upper end portion and said inlet slot, and an outlet slot into which an outlet portion of said elastic tube is inserted to attach said outlet portion to said pump housing is provided, said outlet slot is provided with a lever for pressing said outlet portion into said outlet slot to hold said outlet portion in said outlet slot, said lever being rotated perpendicularly to the axis of said elastic tube by a spring force to press said outlet portion of said elastic tube, an upper end portion of said lever is tilted relative to the vertical axis, said outlet portion is attached to said pump housing by being pushed downward through a place between said upper end portion and said outlet slot.

14. The roller pump according to claim 13, wherein said inlet slot is provided with a lever for pressing said inlet portion into said inlet slot to hold said inlet portion in said inlet slot, said lever being rotated perpendicularly to the axis of said elastic tube by a spring force to press said inlet portion of said elastic tube, an upper end portion of said lever is tilted relative to the vertical axis, said inlet portion is attached to said pump housing being pushed downward through a place between said upper end portion and said inlet slot, said outlet slot is provided with a lever for pressing said outlet portion into said outlet slot to hold said outlet portion in said outlet slot, said lever being rotated perpendicularly to the axis of said elastic tube by a spring force to press said outlet portion of said elastic tube, an upper end portion of said lever is tilted relative to the vertical axis, said outlet portion is attached to said pump housing being pushed downward through a place between said upper end portion and said outlet slot.

15. The roller pump according to claim 13, wherein said driver is a stepping motor provided with a rotation sensor and being roll controllable.

16. The roller pump according to claim 15, wherein said inlet slot is provided with a lever for pressing said inlet portion into said inlet slot to hold said inlet portion in said inlet slot, said lever being rotated perpendicularly to the axis of said elastic tube by a spring force to press said inlet portion of said elastic tube, an upper end portion of said lever is tilted relative to the vertical axis, said inlet portion is attached to said pump housing being pushed downward through a place between said upper end portion and said inlet slot, said outlet slot is provided with a lever for pressing said outlet portion into said outlet slot to hold said outlet portion in said outlet slot, said lever being rotated perpendicularly to the axis of said elastic tube by a spring force to press said outlet portion of said elastic tube, an upper end portion of said lever is tilted relative to the vertical axis, said outlet portion is attached to said pump housing being pushed downward through a place between said upper end portion and said outlet slot.

* * * * *